(12) United States Patent
Burriesci

(10) Patent No.: US 11,918,467 B2
(45) Date of Patent: Mar. 5, 2024

(54) SEMI-RIGID ANNULOPLASTY RING AND METHOD OF MANUFACTURING

(71) Applicant: FONDAZIONE RI.MED, Palermo (IT)

(72) Inventor: Gaetano Burriesci, Palermo (IT)

(73) Assignee: FONDAZIONE RI. MED, Palermo (IT)

(*) Notice: Subject to any disclaimer, the term of this patent is extended or adjusted under 35 U.S.C. 154(b) by 338 days.

(21) Appl. No.: 17/055,290

(22) PCT Filed: May 15, 2019

(86) PCT No.: PCT/IB2019/054029
§ 371 (c)(1),
(2) Date: Nov. 13, 2020

(87) PCT Pub. No.: WO2019/220365
PCT Pub. Date: Nov. 21, 2019

(65) Prior Publication Data
US 2021/0186697 A1    Jun. 24, 2021

(30) Foreign Application Priority Data
May 16, 2018   (IT) .................. 102018000005436

(51) Int. Cl.
*A61F 2/24*  (2006.01)
(52) U.S. Cl.
CPC .... *A61F 2/2445* (2013.01); *A61F 2210/0014* (2013.01); *A61F 2210/0076* (2013.01);
(Continued)
(58) Field of Classification Search
CPC .................. A61F 2/2445; A61F 2/2448; A61F 2210/0014; A61F 2210/0076;
(Continued)

(56) References Cited

U.S. PATENT DOCUMENTS

| 2009/0036979 A1 | 2/2009 | Redmond |
| 2009/0287303 A1 | 11/2009 | Carpentier |

(Continued)

FOREIGN PATENT DOCUMENTS

| JP | 2009539422 | 11/2009 |

OTHER PUBLICATIONS

International Search Report, issued in PCT/IB2019/054029, dated Aug. 22, 2019.
(Continued)

*Primary Examiner* — Brian A Dukert
*Assistant Examiner* — Rebecca Lynee Zimmerman
(74) *Attorney, Agent, or Firm* — Ferguson Case Orr Paterson

(57) ABSTRACT

Annuloplasty prosthesis device (1), which is suitable for remodeling a native annulus (2), comprises a body having the shape of at least one ring portion defining a longitudinal direction, coinciding with or locally parallel to the longitudinal development direction of said body; said portion (5) being opposite to said first arcuate section (4), and the body comprises a first arcuate section (4) and at least a second segment (5); said first arcuate section (4) is flexible in a first direction, locally transverse to the longitudinal direction, so as to be deformable under flexion along said first direction; said first arcuate section (4) defines a plane of storage substantially parallel both to the longitudinal direction and to the first direction; said at least a second section (5) is rigid under flexion in said plane of storage (XY); said second section (5) is flexible in a second direction (ZZ), transverse to the plane of storage, so as to be deformable under flexion along said second direction.

14 Claims, 7 Drawing Sheets

(52) U.S. Cl.
CPC . *A61F 2220/0075* (2013.01); *A61F 2240/001* (2013.01); *A61F 2250/0029* (2013.01)

(58) Field of Classification Search
CPC ........ A61F 2220/0075; A61F 2240/001; A61F 2250/0029; A61F 2230/0015; A61F 2230/0043; A61F 2250/0036
See application file for complete search history.

(56) References Cited

U.S. PATENT DOCUMENTS

| | | |
|---|---|---|
| 2010/0152844 A1* | 6/2010 | Couetil ................ A61F 2/2448 623/2.36 |
| 2010/0168845 A1 | 7/2010 | Wright |
| 2012/0071970 A1 | 3/2012 | Carpentier |
| 2016/0354206 A1 | 12/2016 | McCarthy |

OTHER PUBLICATIONS

Nternational Written Opinion, issued in PCT/IB2019/054029, dated Aug. 22, 2019.

\* cited by examiner

SEMI-RIGID ANNULOPLASTY RING AND METHOD OF MANUFACTURING

FIELD OF THE INVENTION

The present invention relates to an annuloplasty prosthesis device.

In particular, the present invention relates to an annuloplasty prosthesis device for remodeling a native annulus of an atrioventricular valve.

An annuloplasty prosthesis device according to the present invention is particularly suitable, but not uniquely intended, for remodeling a native mitral annulus.

The present invention also relates to a method for manufacturing said annuloplasty prosthesis device.

BACKGROUND ART

The mitral valve is an atrioventricular valve which selectively connects the left atrium and the left ventricle of the heart. The mitral valve is also called the bicuspid valve and comprises two opposite leaflets suitable for occluding the valve lumen. In particular, the mitral valve comprises a usually anterior semicircular leaflet and an elongated back leaflet. The peripheral portions of the two opposite leaflets join together in portions called commissures.

In healthy heart conditions, when the valve is closed, the cantilevered central portions of these leaflets completely occlude the passage lumen and are both folded towards the ventricle, adhering in respective leaflet-to-leaflet contact portions known as coaptation zones. These leaflet-to-leaflet contact portions provide adhesion between the leaflets to ensure the valve is held during the ventricle contraction phase (systole) to avoid mitral regurgitation, i.e. the unwanted reflux of a quantity of blood, during the systole, from the ventricle to the left atrium and then to the lungs which can cause an increase in pulmonary pressure and a reduction in cardiac output.

The mitral valve also comprises the mitral annulus, which forms an anatomical junction between the atrium and the ventricle, defining the passage lumen or orifice between atrium and ventricle, and acts as an anchorage site for the peripheral portions of the valve leaflets. The mitral annulus is basically a continuous ring partially made up of contractile muscle fibers and partially made up of connective fibrous tissue. The three-dimensional shape of the surface defined by the mitral annulus is complex and is comparable to that of a saddle.

In particular, the posterior portion or segment of the annulus surrounds an arc of the lumen passing between the atrium and the ventricle, substantially defining a valve plane oriented in a substantially sub-horizontal direction in a subject when he assumes an upright posture. This posterior portion or segment of the annulus is predominantly made up of contractile muscle fibers.

Instead, the anterior portion or segment of the annulus, i.e. the portion of the annulus facing the subject's sagittal plane when in an upright position, in other words towards the aortic root, rests on a portion of the heart wall facing the left atrium which exhibits a slope substantially cambered, i.e. having humpback shape, placing itself astride thereof. Therefore, said anterior portion of the annulus comprises a segment which is raised with respect to the valve plane defined by the posterior portion of the annulus. This raised anterior segment is curved with a concavity facing downwards and which defines two opposite concavity changes in the proximity of the commissures of the leaflets which impart the characteristic saddle shape to such an anterior portion. This anterior portion or segment is instead mainly made up of fibrous tissue unsuitable for contracting.

From a purely geometric point of view, when the subject is in an upright position, the mitral annulus defines two diametrically opposite peak portions and two depressing portions, also opposite and facing the passage lumen. Typically, the depression portions are located at the commissures of the leaflets and define a depression-depression joining line, while the peak portions of the annulus are identified on the curved anterior segment and on the posterior segment facing it, respectively, defining a peak-peak joining line substantially orthogonal to the above depression-depression joining line.

During systole, the mitral valve is closed and the volume of the left ventricle is reduced to allow the cardiac pump to perform its function of blood ejection. At the same time, the muscular portion or segment of the mitral annulus contracts, while the fibrous portion or segment, in response to the contraction of the muscular portion, passively undergoes a raising and approaching movement relative to the opposite edge of the annulus, a movement driven by the contraction of the muscle fibers of the posterior contractile portion of the annulus itself.

During the diastolic phase, the leaflets of the mitral valve are open due to the overpressure of the left atrium with respect to the ventricle, which is relaxed, and the posterior contractile portion of the annulus is also relaxed and therefore there is an elongation of the posterior muscular segment which causes a countermovement of lowering and relative distancing of the anterior fibrous and posterior muscular portions. The periodic contractions of the annulus cause cyclical dynamics, alternating such a movement with such a countermovement.

The dynamics of the mitral annulus during the cardiac cycle can be modeled as if provided with two opposing hinges located in the proximity of the commissures of the leaflets, which allow to define a sub-transversal or sub-horizontal first plane on which the posterior muscular segment lies, and a second distinct anterior plane incident on the first plane when raising in the depression-depression joining line traceable between the two opposed commissures.

Numerous factors can lead the mitral valve to a state of incomplete closure of the passage lumen, thus favoring the onset of retrograde flows which reduce the output of the heart pump. In particular, the incomplete reclosing of the leaflets causes the non-adhesion of the coaptation zones of the leaflets themselves, always keeping at least one orifice between the atrium and the ventricle open. Therefore, when the ventricle contracts to pump blood in circulation, a fraction of the blood volume passes through the orifice and returns to the atrium, causing the pulmonary pressure to increase which causes a decrease in the cardiac output.

The incomplete reclosing of the valve leaflets can be caused by the dilation of the tissue which forms the mitral annulus, which makes some portions of the annulus itself loose, usually the posterior portions richer in contractile muscle fibers. In this dilated pathological configuration of the annulus, the leaflets are insufficiently extended to completely occlude the passage lumen during systole.

It is generally known to remedy this pathological condition, also known as mitral insufficiency, by implanting a prosthesis. For example, valve prostheses are known which completely replace the native valve.

A reparative technique characterized by less invasiveness, as it does not aim at replacing the entire valve, consists in the implantation of a prosthetic ring designed to repair the function of the annulus, correcting the shape of the passage lumen or orifice so as to restore the effective closure of native mitral valve leaflets. Such a prosthetic ring is typically sutured on the side facing the atrial cavity of the native annulus.

Rigid annuloplasty rings have been proposed, as disclosed for example by U.S. Pat. No. 3,656,185, suitable for providing a constant action to remodel the native annulus and which nevertheless resist to the contractions of the muscle fibers of the annulus, thus preventing the contraction, thereby generating strong stresses localized at the points of suture.

Fully flexible annuloplasty solutions have also been proposed, as shown in U.S. Pat. No. 4,055,861, which however are unsuitable for guiding the remodeling of the native annulus because they are too compliant.

An example of an annuloplasty ring is shown by document U.S. Pat. No. 5,104,407. This solution provides an annular body with the typical oblong shape to define a sort of "D" formed by a bundle of strands wrapped in a sleeve. The annular body comprises arc portions of variable rigidity. In particular, the portion intended to be associated with the fibrous anterior segment of the native annulus has a substantially rectilinear longitudinal extension, forming the right side of the oblong "D" shape of the ring, and is characterized by greater flexion rigidity than the remaining arcuate segments of the prosthetic ring. The rigid portion of the ring is made, for example, by crimping together the wires which make up the strands which form the annular core, so that such individual wires are prevented from sliding on one another in that rigid portion.

Although satisfactory from some points of view, annuloplasty prostheses of the aforementioned type have an excessive local rigidity, which can interfere with the desired functionality of the native annulus, since for example such prosthetic ring is a constraint on the lifting deformation of the fibrous portion. At the same time, such a ring solution has the opposite arcuate segment, intended to interface with the posterior contractile muscular segment of the annulus, extremely yieldable locally. This compliance can be undesirable where the need is felt to obtain a remodeling of the muscular portion of the annulus, which is intrinsically more subject to being subjected to longitudinal dilation of the muscle fibers which compose it. Very often, in fact, the failure of annuloplasty implants is due to localized dehiscence.

A similar solution thus subjected to the same drawbacks is shown in U.S. Pat. No. 5,607,471 where the core has variable cross-sectional portions which give a different flexibility in all deformation directions of the prosthetic ring.

Document U.S. Pat. No. 5,061,277 shows a prosthetic ring solution similar to the above one, where the core consists of two arc segments, one rigid and one flexible, connected at ends thereof at the commissures, forming two opposite mechanical hinges. This solution, in addition to the aforementioned drawbacks, lacks the necessary dynamic continuity of the core structure which could lead to catastrophic overstressing of the two opposite hinges.

US-2010-152844 shows a prosthetic ring solution in which notches are provided which act as hinges on the portions of the ring body which correspond to the trigonal portions of the native valve. These notches are able to make the raised portion of the prosthetic ring more flexible in the horizontal plane, so as to adapt to the deformations of the native annulus during the cardiac cycle and therefore this solution is ineffective in forcing a desired remodeling of the native annulus but, on the contrary, it adapts to the deformations thereof. Moreover, such a solution has a plurality of holes on the ring body intended to receive the suture thread. For these reasons, this solution is extremely complex and expensive to implement and in addition necessarily imposes the concentration of the stresses in the region of the ring body in proximity to and at the notches, which can impose an early failure of the implant, as well as in proximity to holes for the suture thread.

Also known are solutions of annuloplasty ring having a closed-loop core made starting from a shape-memory alloy tube processed by laser removal, in order to return a variously chiseled tubular geometry, rich in openings passing through the core body. Solutions of this type are shown for example in documents EP-1803420, EP-1719476, US-2007-0162112 and are usually rings which offer similar flexibility in all directions. Such solutions therefore do not fully solve the problem of the effectiveness of the remodeling action of the native annulus.

The need is strongly felt to provide an annuloplasty prosthetic ring solution capable of overcoming the drawbacks mentioned above with reference to the prior art.

At the same time, the need is strongly felt to provide an annuloplasty prosthetic ring solution of improved functionality in terms of native annulus remodeling without resulting in decreased reliability as well as increased constructive complexity.

Likewise, the need is felt to provide an annuloplasty prosthetic ring solution made of a reduced number of parts to be assembled, without thereby leading to a decrease in annulus remodeling and reliability of the solution.

Solution

It is an object of the present invention to obviate the drawbacks of the prior art and to provide a solution to the requirements mentioned thus far.

These and other objects are achieved by a device according to claim 1 and by a method according to claim 15.

Some advantageous embodiments are the subject of the dependent claims.

With the proposed solutions, an annuloplasty prosthesis device is provided having portions with locally directional rigidity or flexibility.

With the proposed solutions, an annuloplasty prosthesis device is allowed to provide an improved remodeling action of the native annulus.

A prosthesis device according to the present invention is particularly suitable, but not uniquely intended, for native mitral annulus remodeling.

Preferably, a prosthesis device according to the present invention is suitable for remodeling the native annulus of the tricuspid valve or other valves of the cardiovascular system.

FIGURES

Further features and advantages of the device and of the method according to the invention will be readily apparent from the following description of preferred embodiment examples thereof, provided purely by way of a non-limiting example, with reference to the accompanying figures, in which.

Figure 14A:
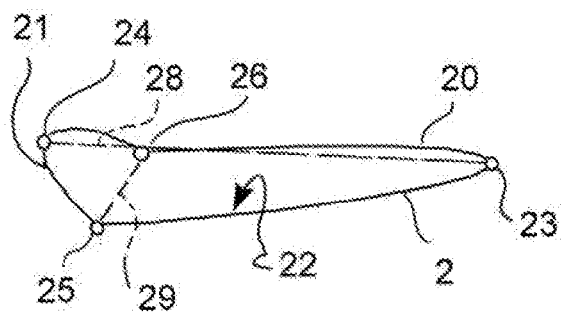
Figure 14B:
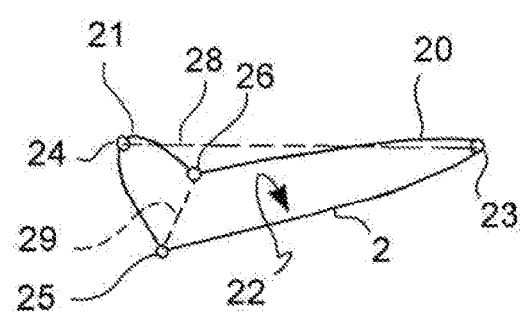

FIGS. 14-a and 14-b schematically show an axonometric view of the three-dimensional conformation of a native mitral annulus during the diastolic phase and during the systolic phase, respectively.

DESCRIPTION OF SOME PREFERRED EMBODIMENT EXAMPLES

According to a general embodiment, an annuloplasty prosthesis device 1 is provided.

The annuloplasty prosthesis device 1 according to the invention is particularly suitable, but not uniquely intended, for the native mitral annulus remodeling, in other words the remodeling of the native annulus 2 of a native mitral valve 13.

The annuloplasty prosthesis device 1 according to the invention is also suitable for native annulus remodeling of a native tricuspid valve 15.

Figure 1:
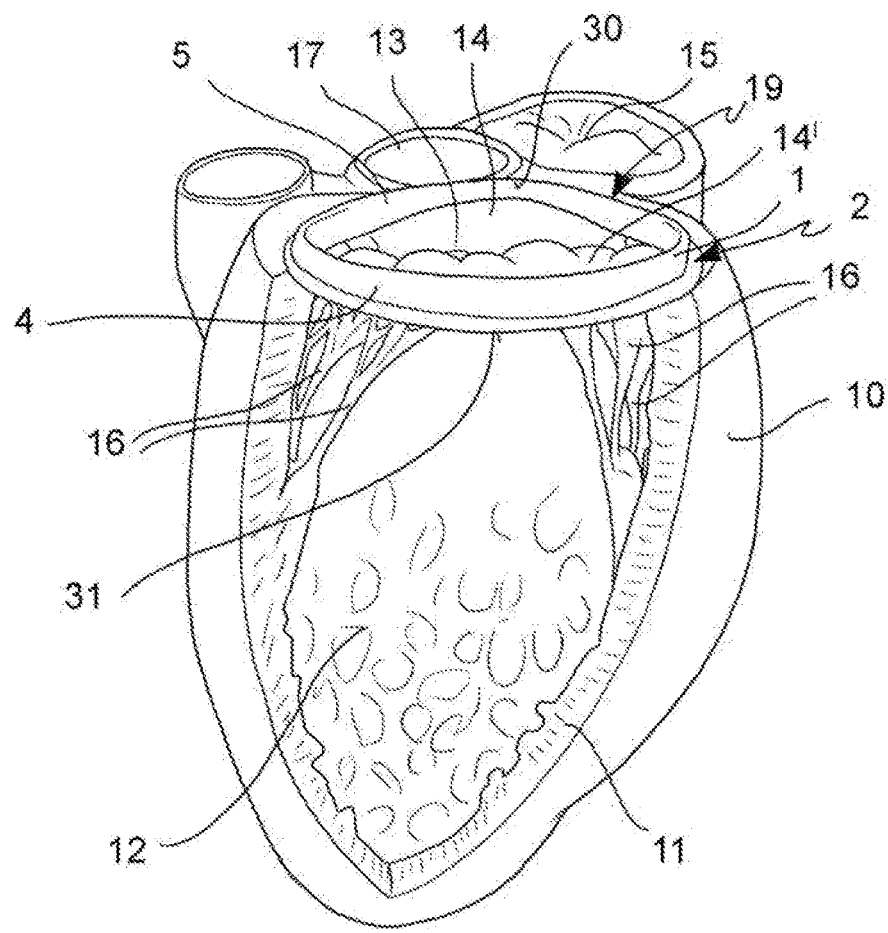
FIG. 1 is an axonometric sectional view of a ventricular chamber of a native heart, wherein an annuloplasty prosthesis device is shown in axonometry, according to an embodiment, when in operating conditions.

As shown for example in FIG. 1, a native heart 10 comprises heart walls 11 which delimit a left ventricular chamber 12 and a left atrial chamber. Said native heart 10 further comprises a native mitral valve 13 comprising a native mitral annulus 2, which delimits a portion of native internal volume 22 selectively occludable by a pair of valve leaflets 14, 14' comprising an anterior valvular leaflet 14 and a posterior valve leaflet 14', as well as chordae tendinae 16 to connect at least one valve leaflet 14, 14' with the heart walls 11 facing the left ventricular chamber 12. The native heart 10 further comprises a tricuspid valve 15 interposed between the right ventricular chamber and the right atrial chamber of the native heart 10. The native heart 10 further comprises an aortic root 17 facing the native aortic valve located at the exit of the left ventricular chamber 12.

Figure 2:
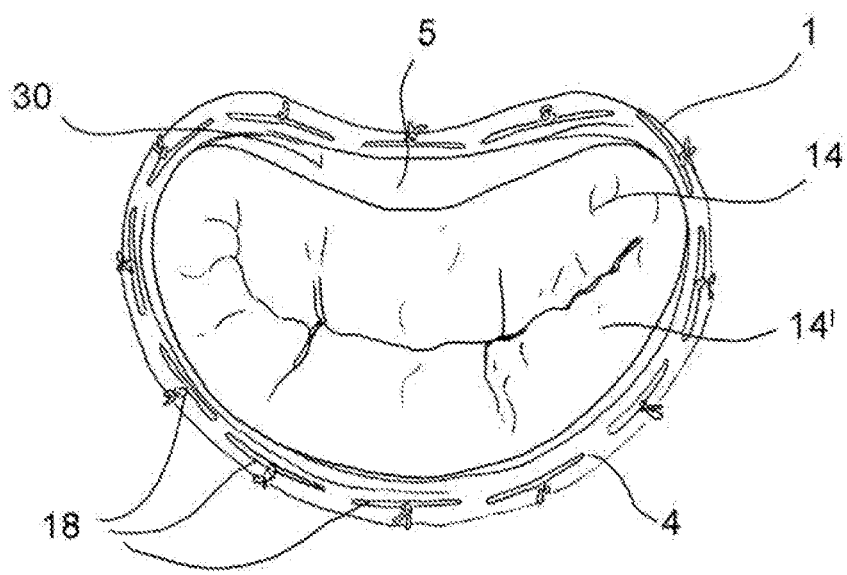
FIG. 2 is a plan view from above of a native mitral valve showing an annuloplasty prosthesis device, according to an embodiment, when in operating conditions.

As shown for example in FIG. 2, the annuloplasty prosthesis device 1 is adapted to be sutured, by means of a surgical suture device 18, to the native mitral annulus 2 on the side of the native mitral annulus facing the left atrial chamber 19.

Said annuloplasty prosthesis device 1 comprises a body having shape of at least a portion of a ring defining a longitudinal direction X-X, coincident with or locally parallel to the longitudinal development direction of said body. According to an embodiment, said body has the shape of at least a portion of a ring surrounding at least partially a prosthesis lumen 6.

Said body comprises a first arcuate segment 4 and at least one second segment 5, opposite said first arcuate segment 4 and preferably facing said first arcuate segment 4. According to an embodiment, said first arcuate segment 4 faces said prosthesis lumen 6, said at least one second segment 5 faces said prosthesis lumen 6, wherein said second segment 5 and said first segment 4 are opposite each other with respect to said prosthesis lumen 6. According to an embodiment, said first arcuate segment 4 and said second segment 5 of the body of the annuloplasty prosthesis device 1 are diametrically opposed.

Preferably, said first arcuate segment 4 is adapted to be sutured to the posterior segment 20 of the native mitral annulus 2. In other words, said first arcuate segment 4 is intended to be sutured to the posterior segment 20 or portion of the contractile native mitral annulus 2.

Preferably, said second segment 5 is adapted to be sutured to the anterior segment 21 of the mitral annulus, i.e. the segment of the mitral annulus near the aortic root 17. In other words, said second segment 5 is intended to be sutured to the anterior segment 21 or portion of the fibrous native mitral annulus 2 and therefore unsuitable for contracting.

According to a preferred embodiment, said first arcuate segment 4 is flexible in a first direction Y-Y, locally transverse to the longitudinal direction X-X along said first arcuate segment 4 and preferably locally orthogonal to the longitudinal direction X-X, so as to be deformable in bending (under flexion) along said first direction Y-Y. Thereby, said first arcuate segment 4 is able to be deformed under flexion when biased under flexion by the deformation of the posterior segment 20 of the native mitral annulus 2. Preferably, said first arcuate segment 4 comprises a curved portion. According to an embodiment, said first arcuate segment 4 is formed by a curved portion of said body.

According to a preferred embodiment, said first arcuate segment 4 is elastically deformable along said first direction Y-Y under flexion.

According to a preferred embodiment, said first arcuate segment 4 defines a lying plane X-Y or resting plane X-Y substantially parallel to both the longitudinal direction X-X and to the first direction Y-Y. In other words, said first arcuate segment 4 is adapted to lie on a lying plane X-Y substantially parallel to both the longitudinal direction X-X and the first direction Y-Y. According to an embodiment, said lying plane X-Y is substantially parallel to at least one sculating circle on the first arcuate segment 4, and preferably to a plurality of oscillating circles to the first arcuate segment 4.

According to a preferred embodiment, said first arcuate segment 4 is elastically deformable in bending (under flexion) in the lying plane X-Y. In this way, said first arcuate segment 4 can flex, thereby deforming, while remaining in the lying plane X-Y, for example by means of accentuating its curvature.

As shown for example in FIGS. 14-a and 14-b, the native mitral annulus 2 has a complex three-dimensional shape, and comprises a rear portion 20 comprising a first peak 23 and a front portion 21 comprising a second peak 24, said peaks 23, 24 being mutually opposite and facing the native internal volume portion 22, and wherein said native annulus 2 further comprises a first depression 25 and a second depression 26, opposite each other and facing the native internal volume portion 22, and wherein said depressions 25, 26 are placed lower than said second peak 24 in a subject when in an upright position, and are preferably placed substantially near the commissures 27 of the valve leaflets 14, 14'. In a native annulus 2, a peak-peak joining line 28 and a depression-depression joining line 29 are defined, which are not parallel and not incident to each other.

According to an embodiment, said first direction Y-Y is directed from said first arcuate segment 4 towards said at least one second segment 5. According to an embodiment, said first direction Y-Y is substantially horizontal or sub-horizontal, when in operating conditions. Thereby, said lying plane X-Y is substantially horizontal or sub-horizontal when in operating conditions.

According to an embodiment, said lying plane X-Y is substantially parallel to the opening-closing direction of the native valve leaflets 14, 14. Due to the provision of said first arcuate segment 4 flexible in the lying plane X-Y, it is possible to reduce the concentration of the stresses at the suturing areas, since the cyclic movement of the posterior portion of the annulus is guided towards, and away from, said opposite second portion 5.

According to an embodiment, said first arcuate segment 4 has a first segment concavity R4 always facing the same direction along the entire longitudinal extension of said first arcuate segment 4. Preferably, the first segment concavity R4 of the first arcuate segment 4 of the body of the annuloplasty prosthesis device 1 faces the prosthesis lumen 6. Preferably, the first segment concavity R4 of the first arcuate segment 4 of the body of the annuloplasty prosthesis device 1 substantially faces said second segment 5.

Advantageously, said at least one second section 5 is rigid in bending (under flexion) in said lying plane X-Y In this way, said second segment 5 is unsuitable for deforming in bending (under flexion) in said lying plane X-Y, even when said first arcuate segment 4 is bent.

Preferably, the term "rigid" is meant to indicate that said second segment 5 has a significantly lower flexibility than the flexibility of the first arcuate segment 4, even though it may bend. In other words, the term "rigid" is not meant to indicate an absolute rigidity, but rather a relative rigidity in relation to the rigidity of the first arcuate segment 4 when evaluated in said lying plane X-Y, although the rigidity could be absolute according to some embodiments.

According to a preferred embodiment, said at least one second section 5 is more rigid in bending (under flexion) in said lying plane X-Y than said first arcuate segment 4 in said lying plane X-Y.

Preferably, said at least one second segment 5 is rigid in bending (under flexion) in said first direction Y-Y. Thereby, said second segment 5 is substantially unsuitable for deforming in bending (under flexion) along said first direction Y-Y, even when said first arcuate segment 4 is bent along said first direction Y-Y.

Due to the provision of said at least one second segment 5 which is substantially rigid and unsuitable for deforming in bending (under flexion) in said lying plane X-Y, the remodeling of the native annulus 2 is favored since, when in operating conditions, said second portion 5 exerts a remodeling action on said anterior segment 21 of the native annulus which resists to the displacement towards, and away from, the posterior segment 20 of the native annulus 2.

Advantageously, said second segment 5 is flexible in a second direction Z-Z, transversal to said lying plane X-Y. In other words, said second direction Z-Z is transversal both to the first direction Y-Y and to the longitudinal direction X-X, so as to be deformable in bending (under flexion) along said second direction Z-Z.

According to a preferred embodiment, said second segment 5 is elastically deformable in bending (under flexion) in said second direction Z-Z transversal to the lying plane X-Y. In this way, said second segment 5 bends out of the lying plane X-Y.

Due to the provision of said second flexible segment in said second direction Z-Z transversal to the lying plane X-Y both to the first direction Y-Y and to the longitudinal direction X-X, said body of said annuloplasty prosthesis device 1 is provided with a directional selective rigidity. In other words, said body of said annuloplasty prosthesis device 1 is provided with a directional selective flexibility aimed at guiding the native anulus remodeling.

Due to the provision of said second flexible segment in said second direction Z-Z transversal to the lying plane X-Y, said body is allowed to guide the lifting movement of the anterior portion 21 of the native annulus 2 when in operating conditions during the systole. Likewise, due to the provision of said second flexible segment in said second direction Z-Z, said body is allowed to guide the lowering movement of the anterior portion 21 of the native annulus 2 when in operating conditions during the diastole.

According to a preferred embodiment, said second direction Z-Z forms a predefined angle α with said lying plane X-Y. Preferably, said predetermined angle α is comprised from 20° (degrees) to 160°, and preferably from 30° to 150°, and more preferably from 45° to 135°. According to an embodiment, said predefined angle α is substantially equal to 90°. The choice of the predefined angle α depends on the desired dynamic properties of directional selective rigidity that the annuloplasty prosthesis device 1 will have when it is implanted.

In this way, when said first arcuate segment 4 rests on said lying plane X-Y, said second segment 5 is deformable in bending (under flexion) in a direction transversal to said lying plane X-Y, for example outgoing or entering from the lying plane X-Y or one of the extensions thereof. Preferably, the term "or an extension thereof" is meant to indicate the coplanar extension of the lying plane X-Y outside the portion of the plane delimited by the first arcuate segment 4.

According to an embodiment, the term "lying plane" indicates not only a geometric abstraction, but also the plane on which the first arcuate segment 4 of the annuloplasty prosthesis device 1 rests, when considered alone. In other words, by resting said first arcuate segment 4 of said annuloplasty prosthesis device 1 on a support plane, said support plane is parallel to said lying plane X-Y.

According to a preferred embodiment, said first arcuate segment 4 is rigid in said second direction Z-Z. According to a preferred embodiment, said first arcuate segment 4 is more rigid in bending (under flexion) than said second portion 5 in said second direction Z-Z.

The provision of said first rigid arcuate segment 4 in said second direction Z-Z transversal to the lying plane X-Y, particularly when provided in combination with the provision of said first flexible arcuate segment 4 along said first direction Y-Y, allows to provide said body of the annuloplasty prosthesis device 1 with a distributed directional selective rigidity.

Preferably, the term "rigid" is meant to indicate that said first arcuate segment 4 has a flexibility along the second direction Z-Z which is significantly less than the flexibility along the second direction Z-Z of the second segment 5, even though it may bend. In other words, the term "rigid" is not meant to indicate an absolute rigidity, but rather a relative rigidity in relation to the rigidity of the second segment 5 when evaluated along the second direction Z-Z, although the rigidity could be absolute according to some embodiments.

The joint provision of said first flexible arcuate segment 4 in the lying plane X-Y and rigid along the second direction Z-Z, and of said second segment 5 rigid in the lying plane X-Y and flexible along the second direction Z-Z, allows to obtain an annuloplasty prosthesis device 1 with selective directional rigidity along two or more transverse directions.

Such an annuloplasty prosthesis device 1 allows to guide the movement of the native mitral annulus 2 both during the systolic phase and during the diastolic phase while allowing to model the shape of the native mitral annulus 2 towards a healthy shape, i.e. preventing the posterior segment 20 of the native annulus 2 from deforming too much in enlargement, thus being unsuitable for keeping the valve leaflets 14, 14' tightened during systole.

According to an embodiment, said first arcuate segment 4 and said at least one second segment 5 are flexible independently of one another, preferably along directions which are incident to one another.

According to an embodiment, said at least one second segment 5 is arcuate. In other words, according to an embodiment, said second portion 5 defines a curved longitudinal path defining a second segment concavity R5. Preferably, said second segment concavity faces the lying plane X-Y which crosses the first arcuate segment 4.

According to an embodiment, said body of the annuloplasty prosthesis device 1 further comprises two opposite joining segments 7, 8, comprising a first joining segment 7 and a second joining segment 8 opposite the first joining segment 7, wherein each joining segment 7 or 8 connects said first arcuate segment 4 and said at least one second segment 5 together along said longitudinal direction X-X of the body of the annuloplasty prosthesis device 1.

According to an embodiment, each joining segment 7, 8 comprises at least one curved segment having joining segment concavity R7 or R8 facing towards said at least one second segment 5. Preferably, said joining segment concavity R7, R8 faces the left atrial chamber when in operating conditions. In other words, the joining segment concavity R7, R8 is directed in an outgoing direction from the lying plane X-Y. According to an embodiment, the joining segment concavity R7, R8 faces out of the lying plane X-Y.

According to an embodiment, the second segment concavity R5 is opposite the joining segment concavity R7 or R8.

According to a preferred embodiment, said first arcuate segment 4 has an extension in the longitudinal direction X-X greater than the longitudinal extension of the second segment 5. According to an embodiment, said first arcuate segment 4 has an extension in the longitudinal direction X-X greater than the longitudinal extension of the saddle portion 9. According to an embodiment, said first arcuate segment 4 has an extension in the longitudinal direction X-X at least equal to half of the longitudinal extension of the body of the annuloplasty prosthesis device 1.

According to a preferred embodiment, said second segment 5, said first joining segment 7 and said second joining segment 8 define an open annular path along the longitudinal direction X-X defining a saddle portion 9 comprising at least one change of concavity 32 or flexion portion 32. Preferably, said saddle portion 9 is adapted to lie on the anterior portion 21 of the native mitral annulus 2, which has a saddle-shaped anatomy. Preferably, said saddle portion 9 extends out of the lying plane X-Y, preferably when in undeformed condition. Preferably, by resting said first arcuate segment 4 of said annuloplasty prosthesis device 1 on a support surface, said saddle portion 9 exits from said lying plane X-Y.

According to an embodiment, said saddle portion 9 comprising said second segment 5 substantially lies in the lying plane X-Y, so that when in operating conditions, said saddle portion 9 is adapted to extend out of the lying plane X-Y when moved, preferably pushed, by the displacement of the anterior segment 21 of the native annulus 2 towards said front portion 20 of the native annulus 2 itself. In other words, the saddle portion 9, when under undeformed conditions, substantially lies on the lying plane X-Y.

According to an embodiment, said first arcuate segment 4 is connected in two portions thereof to said at least one second segment 5, along the longitudinal direction X-X.

According to an embodiment, the body of the annuloplasty prosthesis device 1 defines a first side, or atrium-facing side 30, and a second opposite side, or ventricle-facing side 31, opposite the atrium-facing side 30, and adapted to face the native annulus 2 when in operating conditions.

According to a preferred embodiment, said body of the annuloplasty prosthesis device 1 defines a closed ring. In other words, traveling along said body in the longitudinal direction X-X starting from said first arcuate segment 4 in a given direction of travel, said first arcuate segment 4 is cyclically encountered.

Figure 3:
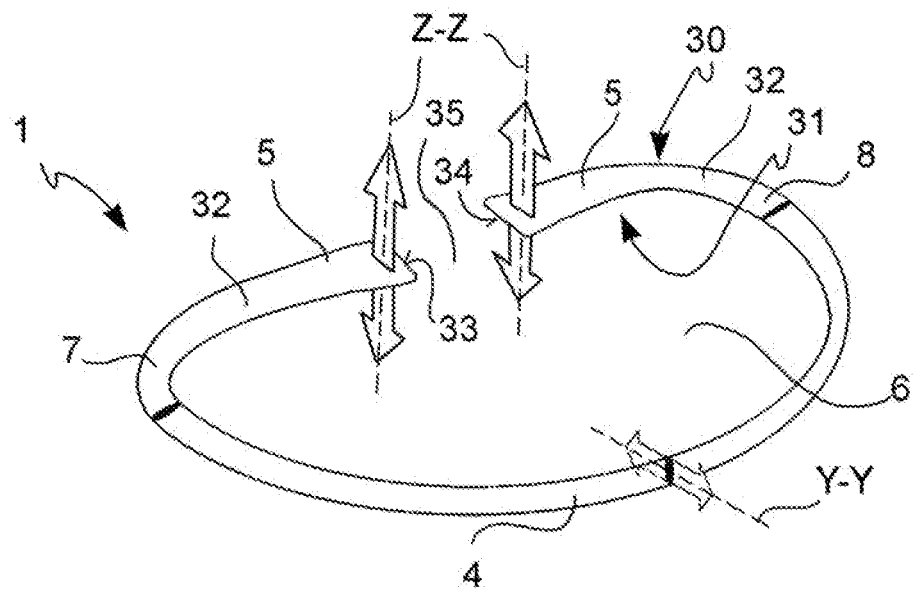
FIG. 3 is an axonometric view of an annuloplasty prosthesis device according to an embodiment.
Figure 4:
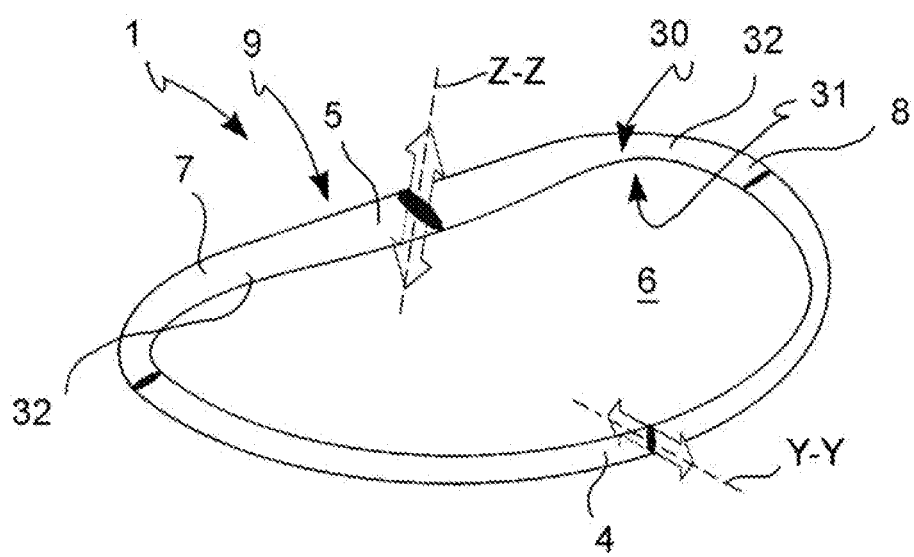
FIG. 4 is an axonometric view of an annuloplasty prosthesis device according to an embodiment.
Figure 5:
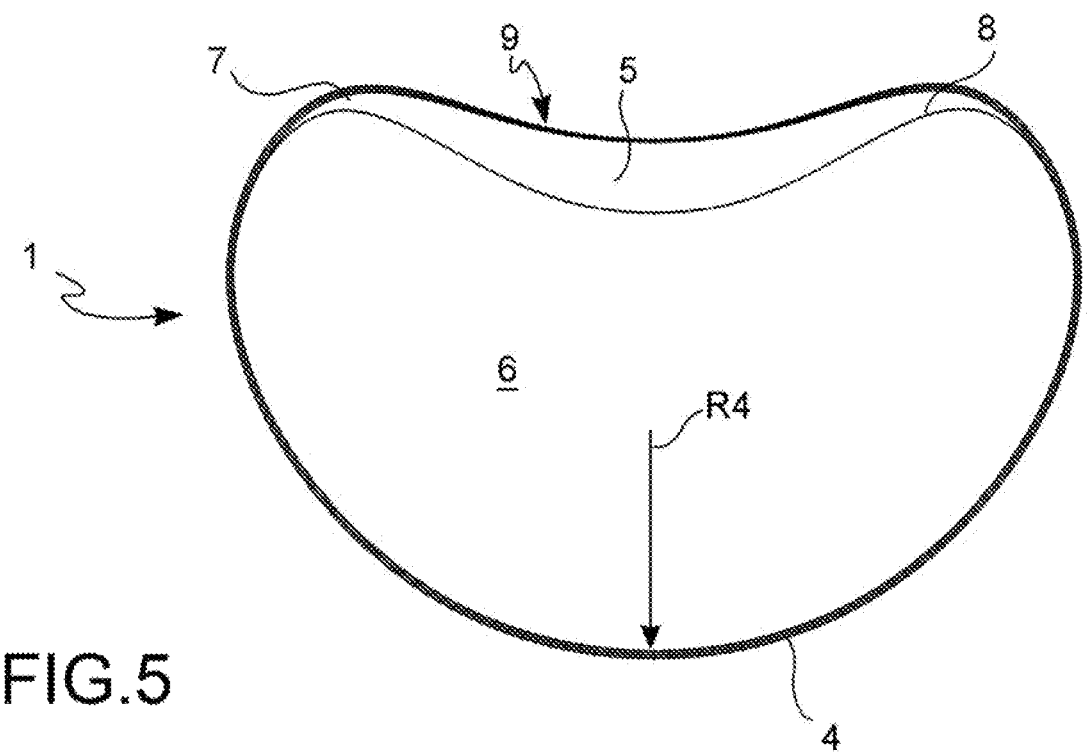
FIG. 5 is a plan view from above of an annuloplasty prosthesis device, according to an embodiment.
Figure 6:
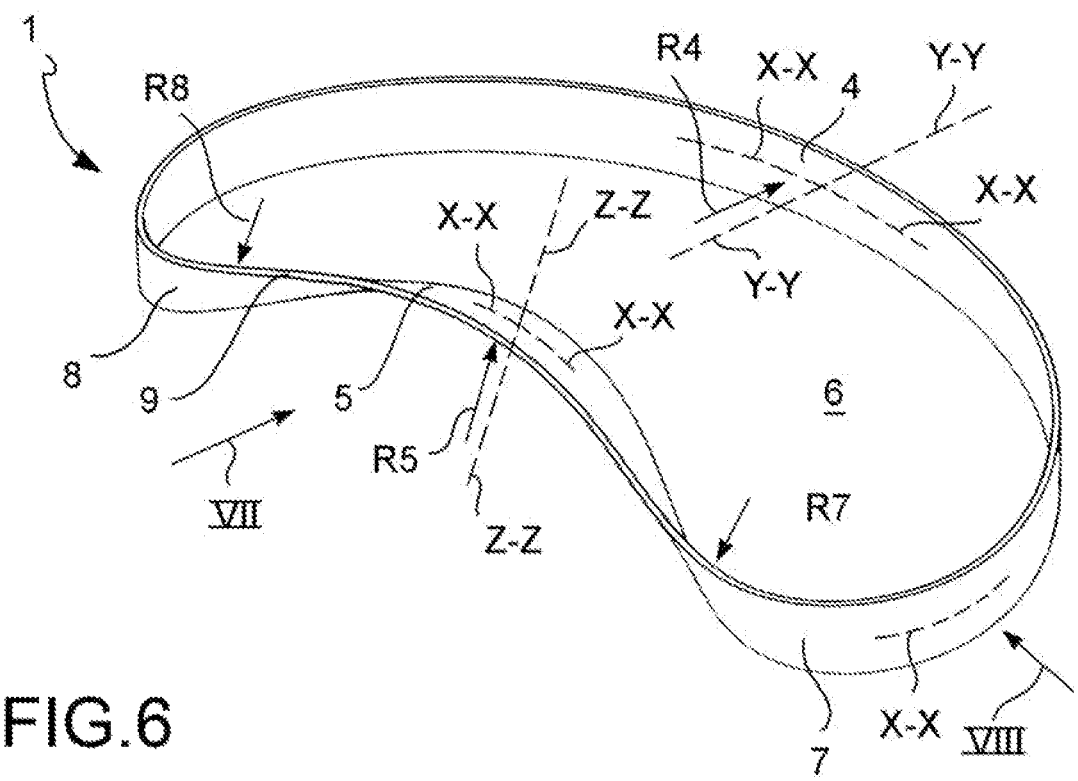
FIG. 6 is an axonometric view of the annuloplasty prosthesis device as shown in FIG. 5.
Figure 7:
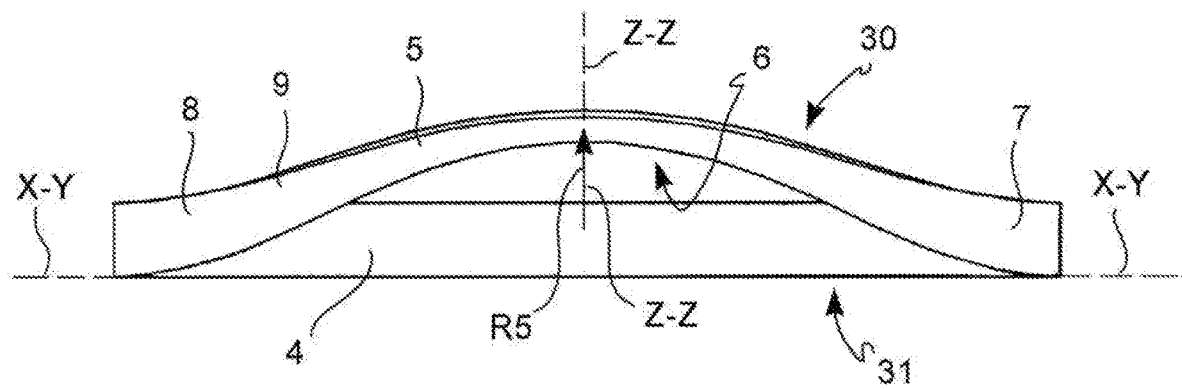
FIG. 7 is a vertical elevation view of the annuloplasty prosthesis device shown in FIG. 6, according to the point of view indicated with the arrow VII in FIG. 6.

According to an embodiment variant shown for example in FIG. 3, said body of the annuloplasty prosthesis device 1 defines a partially closed loop path, in other words an open ring, which embraces said prosthesis lumen 6. Preferably, said body in the form of an open ring comprises two body ends 33, 34, preferably two free cantilevered body ends 33, 34, said two body ends 33,34 being opposite with respect to the body along the longitudinal direction X-X. Preferably, said two body ends 33, 34 face each other defining an interspace 35 there between which opens from the prosthesis lumen 6. According to an embodiment, each body end 33 or 34 of said two body ends 33, 34 is located in a respective second segment 5 of the body. In other words, according to an embodiment, said body comprises two second segments 5, each connected directly or indirectly, by means of a respective joining segment 7 or 8, to the first arcuate segment 4, wherein each of said two second segment 5 comprises a respective end portion 33 or 34. In this way, said end portions 33, 34 are flexible along the second direction Z-Z and rigid in the lying plane X-Y.

According to an embodiment, the flexural strength of said first arcuate segment 4 in the lying plane X-Y is less than the flexural strength of said first arcuate segment 4 along the second direction Z-Z or outside the lying plane X-Y. According to an embodiment, the flexural strength of said second segment 5 in the lying plane X-Y is greater than the flexural strength of said second segment 5 along the second direction Z-Z or outside the lying plane X-Y.

According to an embodiment, said annuloplasty prosthesis device 1 comprises a core 3, which confers the rigidity and the flexibility properties to the body of the annuloplasty prosthesis device 1.

Preferably, said annuloplasty prosthesis device 1 further comprises a coating which coats said core 3. According to an embodiment, said coating comprises a fabric layer 36, for example made of polyester, said fabric layer 36 comprising a suture flange 37 suitable for forming a support for a suturing device 18 for implanting said annuloplasty prosthesis device 1 on said native heart 10.

According to an embodiment, said coating comprises a protective sheath layer 38, for example made of silicone or the like, which coats the core. According to an embodiment, said fabric layer 36 covers said protective sheath 38.

According to an embodiment, the flexural strength of said first arcuate segment 4 in the lying plane X-Y is substantially equal to the flexural strength of said second segment 5 along the second direction Z-Z. In other words, the flexibility of said first arcuate segment 4 in the lying plane X-Y is substantially equal to the flexibility of said second segment 5 along the second direction Z-Z. In other words, the directional rigidity of said first arcuate segment 4 in the lying plane X-Y is substantially equal to the directional rigidity of said second segment 5 in said second direction Z-Z.

According to an embodiment, said body of the annuloplasty prosthesis device 1 has a transverse section, transverse to the longitudinal direction X-X, substantially of the same shape and of the same size along the whole longitudinal extension of said body of the annuloplasty prosthesis device 1.

According to an embodiment, said body has a substantially rectangular cross-section having a first cross-section dimension 39 and a second cross-section dimension 40, substantially orthogonal to said first cross-section dimension 39, wherein said first cross-section dimension 39 is greater than said second cross-section dimension 40. In this way, said body has substantially the shape of a band. In other words, said body has substantially the shape of a ribbon or a lamella. In other words, said body has substantially the shape of a strip. In this way, said body has a first cross-section S4 in said first arcuate segment 4 and a second cross-section S5 in said second segment 5, in which each of said cross-sections S4, S5 has one dimension much greater than the other.

According to a preferred embodiment, said cross-section of said first arcuate segment 4 and the cross-section of said second segment 5 measure the same area.

According to a preferred embodiment, the cross-section S4 of said first arcuate segment 4 and the cross-section S5 of said second segment 5 have the same shape and the same area measurement and are mutually inclined by a twist angle β.

Figure 8:
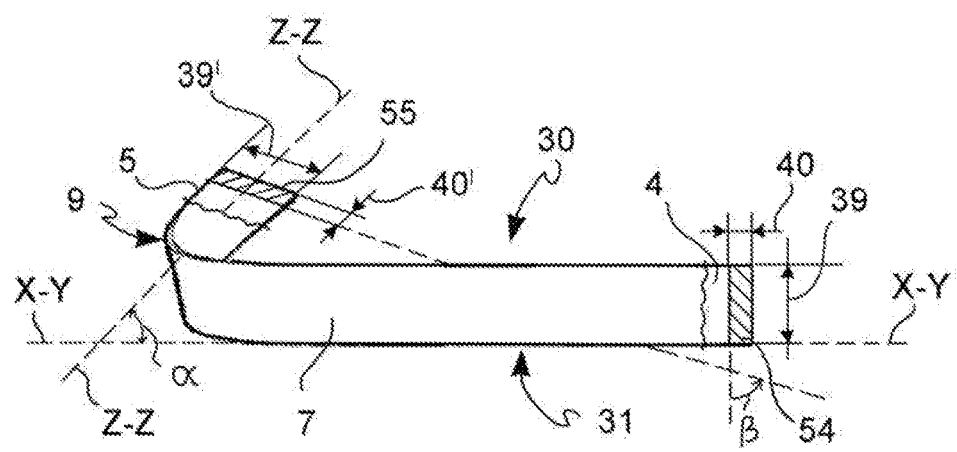
FIG. 8 is a vertical elevation view of the annuloplasty prosthesis device shown in FIG. 6, according to the point of view indicated with the arrow VIII in FIG. 6, in which some parts are sectional for clarity.
Figure 9:
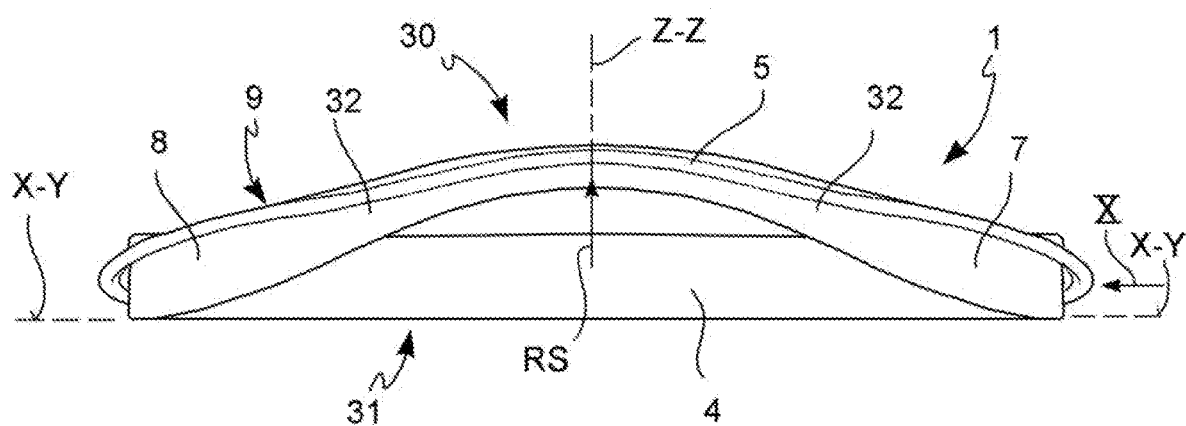
FIG. 9 is a vertical elevation view of an annuloplasty prosthesis device according to an embodiment.
Figure 10:
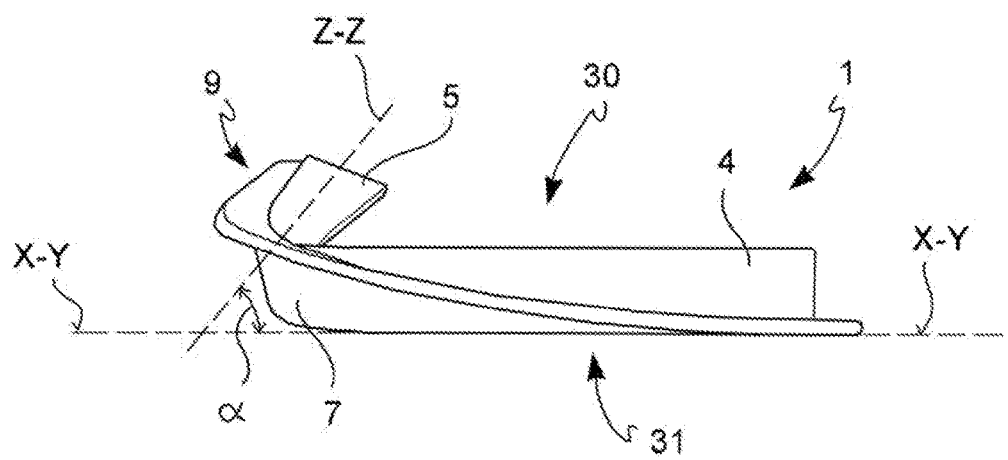
FIG. 10 is a vertical elevation view of the annuloplasty prosthesis device shown in FIG. 9, according to the point of view indicated with the arrow X in FIG. 9.
Figure 11:
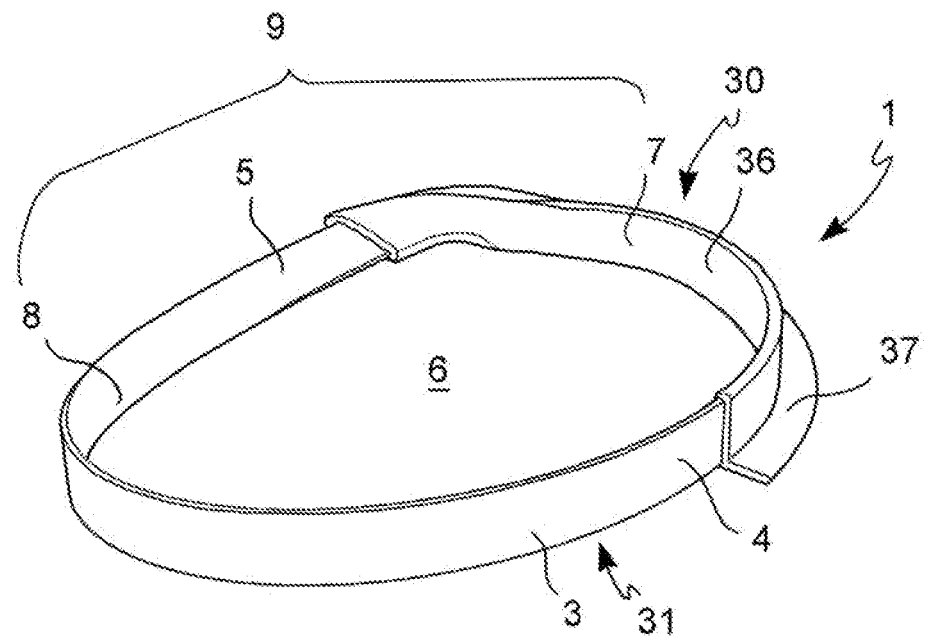
FIGS. 11 and 12 are axonometric views of an annuloplasty prosthesis device, according to some embodiments, wherein the core is illustrated.
Figure 12:
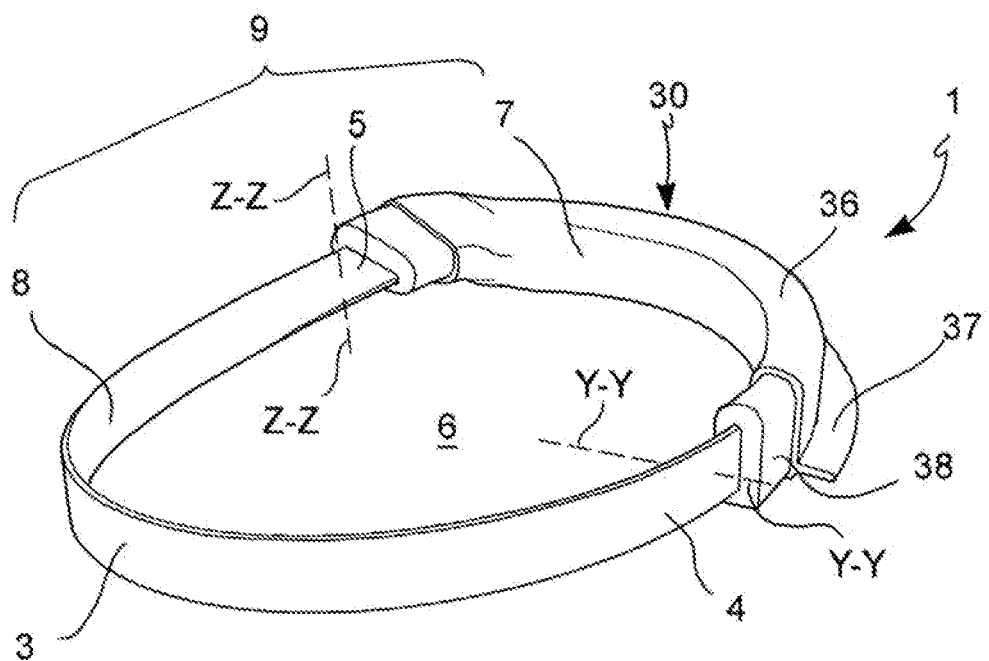

According to a preferred embodiment, as shown for example in FIG. 8, the first cross-section S4 of said first arcuate segment 4 and the second cross-section S5 of said second segment 5 both have a first cross-section dimension 39, 39' and a second cross-section dimension 40, 40' substantially perpendicular to said first cross-section dimension 39, 39', wherein said first cross-section dimension 39, 39' is greater than said second cross-section dimension 40, 40' and wherein said first cross-section dimension 39 evaluated in the first arcuate segment 4 forms a twisting angle β with respect to the first cross-section dimension 39' evaluated in the second segment 5, although said cross-sections S4, S5 may measure the same area.

According to an embodiment, said body is in the form of a twisted or turned band, so that the transverse orientation of said second segment 5 is inclined by a twist angle β with respect to the transverse orientation of said first arcuate segment 4.

In this way, the ventricle-facing side 31 of said annuloplasty prosthesis device 1 is suitable for facing said native annulus 2 portions or segment of different width transverse to the longitudinal direction X-X, and preferably a first arcuate segment of smaller transverse width and a second segment of greater transverse width.

Preferably, said twist angle β is substantially equal to the predefined angle α.

According to an embodiment, the moment of inertia along the first direction Y-Y of said first cross-section S4 of the first arcuate segment 4 is greater than the moment of inertia along the second direction Z-Z of said first cross-section S4 of the first arcuate segment 4.

According to an embodiment, the moment of inertia along the first direction Y-Y of said second cross-section S5 of the second segment 5 is smaller than the moment of inertia along the second direction Z-Z of said second cross-section S5 of the second segment 5.

Figure 13:
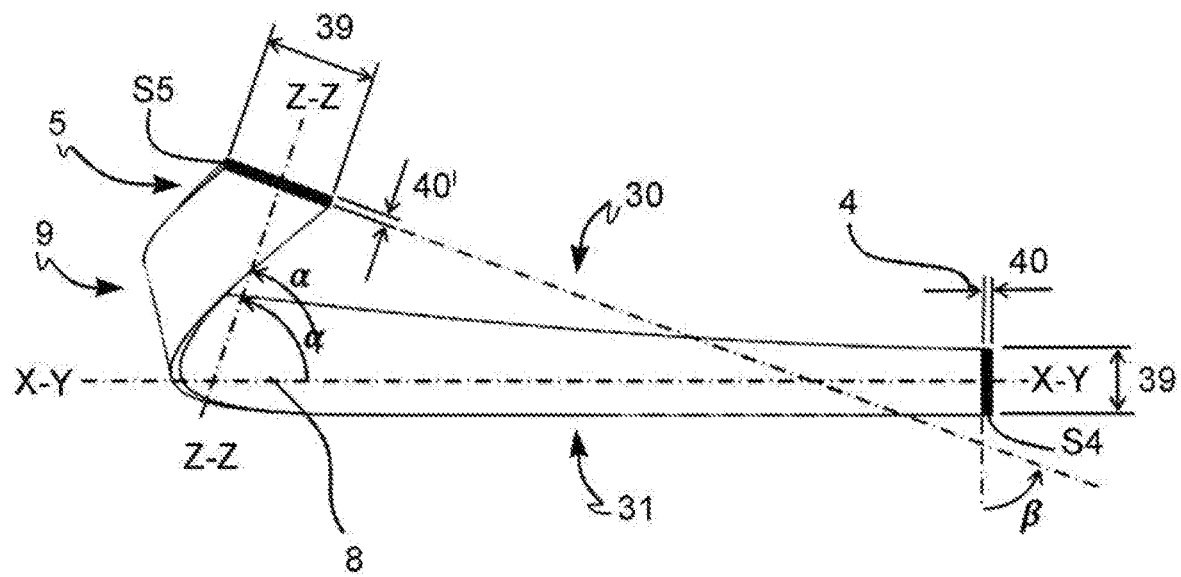
FIG. 13 is a sectional view of the annuloplasty prosthesis device, according to an embodiment, wherein the section is made along a cutting plane orthogonal to the lying plane of the annuloplasty prosthesis device.

According to an embodiment shown for example in FIG. 13, said body of the annuloplasty prosthesis device 1 has a cross-section, transverse to the longitudinal direction X-X, variable along the longitudinal extension of said body. Preferably, the first arcuate segment 4 comprises a narrower cross-section than the second segment 5. Preferably, the sides of the cross-section are mutually non-parallel and convergent or tapered away from said second segment 5 and/or from said saddle portion 9 of the body of the annuloplasty prosthesis device 1.

According to an embodiment, the body of the annuloplasty prosthesis device 1 has a substantially symmetrical shape with respect to a definable symmetry plane. Preferably, said definable symmetry plane intersects said body of the annuloplasty prosthesis device 1 both in said first arcuate segment 4 and in said second segment 5. Preferably, said definable symmetry plane is orthogonal to the lying plane X-Y.

According to an embodiment, said core 3 is made of a tubular element, made for example of nitinol and/or other biocompatible material, processed by machining, for example by laser machining, to form a plurality of cells or meshes which a longitudinal direction X-X is followed along at least a portion of the longitudinal extension of said body, and preferably along the entire longitudinal extension of said body, and even more preferably, said first arcuate segment 4 and said second segment 5 each comprise cells or meshes suitable for providing directional selective rigidity. For example, the meshes of said plurality of meshes are linked with links adjacent thereto along the longitudinal direction, to form at least one portion of said core 3.

According to an embodiment, said core 3 is made of a plurality of cables or wires intertwined to form a strand. Preferably, each of said first arcuate segment 4 and said second segment 5 comprises means for fastening, for example welding and/or crimping, between adjacent cables or wires of said plurality of cables or wires to prevent the relative sliding thereof locally in a certain direction. For example, said first arcuate segment 4 comprises means for securing adjacent cables or wires of said plurality of cables or wires suitable for preventing the relative sliding thereof along a direction transverse to the lying plane X-Y. For example, said second segment 5 comprises means for securing adjacent cables or wires of said plurality of cables or wires suitable for preventing the relative sliding thereof along a direction transverse to the lying plane X-Y.

According to an embodiment, the core 3 is made of a plurality of lamellae or bands or ribbons arranged side by side. Preferably, each of said first arcuate segment 4 and said second segment 5 comprises means for fastening, for example welding and/or crimping, between adjacent lamellae or bands or ribbons of said plurality of lamellae or bands or ribbons to prevent the relative sliding thereof locally in a certain direction. For example, said first arcuate segment 4 comprises means for fastening between adjacent lamellae or bands or ribbons of said plurality of lamellae or bands or ribbons, so as to prevent the relative sliding thereof along a direction transverse to the lying plane X-Y. For example, said second segment 5 comprises means for fastening between adjacent lamellae or bands or ribbons of said plurality of lamellae or bands or ribbons, so as to prevent the relative sliding thereof along a direction transverse to the lying plane X-Y.

According to an embodiment, said core 3 is formed in part by lamellae or bands or ribbons, and/or in part by cables or wires intertwined to form a strand, and/or in part by adjacent meshes or cells, and/or combinations thereof. In this way, it is possible to further improve the directional rigidity properties of the annuloplasty prosthesis device 1.

For example, said core 3 comprises at least one first portion, made of a plurality of lamellae or bands or ribbons placed side by side, and at least one second portion, made of cables or wires intertwined to form a strand. Preferably, said at least one first portion and said at least one second portion are connected or fixed so as to form said core 3.

For example, said core 3 comprises at least one first portion, made of a plurality of lamellae or bands or ribbons placed side by side, and at least one second portion, made of a single lamella or band or ribbon. Preferably, said single band is made in a single piece with at least another band of said plurality of bands of the first portion of the core 3.

According to an embodiment, said core 3 is made in a single piece. In this way, the number of parts and components which form said core 3 of the annuloplasty prosthesis device is reduced.

According to an embodiment, said first arcuate segment 4 is formed at least partially by a leaf spring, so as to be adapted to elastically bias the rear portion 20 of the native annulus 2 in remodeling. In other words, said first arcuate segment 4 is formed at least partially by a leaf spring so as to elastically bias on said rear portion 20 of the native annulus 2 for making it to regain the shape of a healthy annulus, when in operating conditions. For example, said first arcuate segment 4 when bent exerts a preloading action for resisting the deformation of the native annulus 2, and particularly for mitigating the deformation of the posterior contractile muscular portion of the native annulus 2.

According to an embodiment, said second segment 5 is formed at least partially by a leaf spring, so as to be adapted to elastically bias in remodeling said anterior portion 21 of the native annulus 2. In other words, said second segment 5 is formed at least partially by a leaf spring, so as to elastically bias said anterior portion 21 of the native annulus 2 for the purpose of restoring the shape of a healthy annulus, when in operating conditions. For example, said second segment 5 when bent exerts a preloading action for resisting the deformation of the native annulus 2, and particularly for mitigating the deformation of the fibrous anterior portion of the native annulus 2.

According to an embodiment, said core 3 comprises any of the features described above with reference to said body of the annuloplasty prosthesis device 1.

According to an embodiment, said core 3 coincides identically with said body.

A method of manufacturing an annuloplasty ring prosthesis 1 will be described below.

According to a general embodiment, a method of manufacturing an annuloplasty ring prosthesis 1 comprises the following steps:

providing a body to be processed of annular shape, having a predefined cross-section, preferably constant along the entire longitudinal extension of the body to be processed, and comprising a first arcuate segment 4;

twisting at least a portion of said body to be processed of annular shape to obtain a second segment 5, in which the cross-section S5 of said second segment 5 is inclined by a twisting angle β with respect to the cross-section S4 of the first arcuate segment.

In this way, the body of the annuloplasty prosthesis device 1 comprises at least one portion partially twisted or wound around the axis of longitudinal development of the body, and preferably two opposite twisted or wound portions.

Preferably, said cross-section S4 of the first arcuate segment 4 is substantially of the same area measurement as the cross-section S5 of the second segment 5. According to an embodiment, the cross-sections of said joining portions 7, 8 comprise a twist-deformed portion, preferably by plastic deformation, and more preferably by thermoforming. For example, said body of the annuloplasty device 1 is made of superelastic alloy, such as nitinol, and at least said torsionally deformed portions are made by hot-forming. For example, the cross-section of said twist-deformed portion comprises a first dimension 39 which is longer than the first dimension 39 of the cross-section S5 of the second arcuate segment 5 or of the cross-section S4 of the first segment 4. For example, the cross-section of said twist-deformed portion comprises a first dimension 39 having at least one portion curved in a direction locally orthogonal to the longitudinal direction X-X.

According to a possible mode of operating, said twisting step is performed by winding said body around its own longitudinal development axis by a predefined angular quantity substantially equal to said twisting angle 3. Preferably, said predefined angular quantity is less than 90°.

According to a possible mode of operating, said body to be processed is in the form of a cylinder, preferably squat or having height less than the diameter, and said first arcuate segment 4 is an arc of the wall of said cylinder.

According to a possible mode of operating, said body to be processed is in the form of a disc and said first arcuate segment 4 is an arc of the edge of said disc.

According to a possible mode of operating, said predefined cross-section of said body is substantially constant along the entire longitudinal extension of said body.

According to a possible mode of operating, the twisting step is performed by using a twisting tool suitable for pressing on said body to obtain said second segment 5 with a curved surface, preferably cylindrical or spherical.

According to a possible mode of operating, the twisting step is carried out by progressively twisting a portion of said opposite body and facing said first arcuate segment 4.

According to an embodiment variant, a method of manufacturing an annuloplasty ring prosthesis 1 comprises the following steps:

providing an annular-shaped workpiece having a predefined cross-section and comprising at least one second segment 5;

twisting at least a portion of said annular-shaped workpiece to obtain a first arcuate segment 4, in which the cross-section S4 of said first arcuate segment 4 is inclined by a twisting angle β with respect to the cross-section S5 of the second segment.

By virtue of the features described above, provided either separately or jointly together in particular embodiments, it is possible to obtain a device which at the same time meets the above-described contrasting needs and the above-mentioned desired advantages, and in particular:

- it is possible to provide an annuloplasty prosthesis device particularly suitable for guiding the native annulus remodeling where it is implanted, forcing the annulus to deform as it should deform if it were in healthy condition;
- an annuloplasty prosthesis device with directional selective rigidity and flexibility is provided;
- directional selective flexibility properties are provided to said annuloplasty prosthesis device, suitably designed to favor the native anulus remodeling;
- a solution of improved functionality is provided with respect to known solutions, without resulting in an increased constructive complexity;
- for example, joints or hinges are avoided, as well as grooves and slits in order to regulate the localized rigidity of the body of the prosthetic ring and which could generate stress concentration zones;
- the entire body of the prosthetic ring, as well as the core, is allowed to contribute to the localized rigidity and directional flexibility properties, obtaining a substantially continuous distribution of the mechanical properties on the body of the prosthetic ring;
- it allows the core of the prosthetic ring to be kept as compact as possible;
- at the same time, a simpler manufacturing solution is provided with respect to known solutions, without resulting in diminished functionality.

Those skilled in the art may make several changes and adaptations to the embodiments described above and replace elements with others which are functionally equivalent in order to meet incidental and specific needs, without departing from the scope of the following claims.

REFERENCE LIST

1 Annuloplasty prosthesis device
2 Native annulus
3 Core of the prosthesis device
4 First arcuate segment
5 Second segment
6 Prosthetic lumen
7 First joining segment
8 Second joining segment
9 Saddle portion
10 Native heart
11 Heart wall
12 Ventricular chamber
13 Native mitral valve
14 Native front leaflet
14' Native rear leaflet
15 Tricuspid valve
16 Tendon cords
17 Aortic root
18 Suture device
19 Side facing the atrial chamber
20 Posterior portion or posterior segment of the native annulus
21 Anterior portion or anterior segment of the native annulus
22 Portion of native internal volume
23 First peak or peak of the posterior portion of the native annulus
24 Second peak or peak of the anterior portion of the native annulus
25 First depression of the native annulus
26 Second depression of the native annulus
27 Commissure of the native leaflets
28 Peak-peak joining line
29 Depression-depression joining line
30 Atrium-facing side of the prosthesis device
31 Ventricle-facing side of the prosthesis device
32 Change of concavity or flexion portion
33, 34 Body end
35 Interspace
36 Coating fabric layer
37 Coating flange
38 Protective sheath of the coating
39, 39' First cross-section dimension
40, 40' Second cross-section dimension
R4 Concavity of the first arcuate segment
R5 Concavity of the second segment
R7, R8 Joining segment concavity
X-X Longitudinal direction
Y-Y First direction or first cross direction
X-Y Lying plane or support surface of the first arcuate segment
Z-Z Second direction or second cross direction
α Predefined angle
β Twisting angle

The invention claimed is:

1. An annuloplasty prosthesis device, suitable for native annulus remodeling, comprising a body having a shape of at least one portion of a ring defining a longitudinal direction (X-X), coincident with or locally parallel to the longitudinal development direction of said body, wherein:
   said body comprises a first arcuate segment and at least one second segment, opposite said first arcuate segment;
   said first arcuate segment is flexible in a first direction (Y-Y), locally transverse to the longitudinal direction (X-X) along said first arcuate segment, so as to be deformable in bending along said first direction (Y-Y);
   said first arcuate segment defines a lying plane (X-Y) substantially parallel to both the longitudinal direction (X-X) and the first direction (Y-Y);
   said at least one second segment is more rigid under flexion than said first arcuate segment in said lying plane (X-Y); and
   said second segment is flexible in a second direction (Z-Z), transverse to the lying plane (X-Y), so as to be deformable in bending along said second direction (Z-Z), providing directional selective flexibility to said annuloplasty prosthesis device for the purpose of guiding the native annulus remodeling;
   wherein said body is in a form of a twisted band, so that a transverse orientation of said second segment is inclined by a twist angle (β) with respect to a transverse orientation of said first arcuate segment.

2. The annuloplasty prosthesis device of claim 1, wherein said first arcuate segment is more rigid under flexion in said second direction (Z-Z) than said second segment.

3. The annuloplasty prosthesis device of claim 1, wherein said first arcuate segment and said at least one second segment are flexible independently of each other.

4. The annuloplasty prosthesis device of claim 1, wherein a cross-section of said first arcuate segment and a cross-section of said second segment have same shape and area measurement and are mutually inclined by a twist angle (β).

5. The annuloplasty prosthesis device of claim 1, wherein the moment of inertia along the first direction (Y-Y) of said first cross-section of the first arcuate segment is greater than the moment of inertia along the second direction (Z-Z) of said first cross-section of the first arcuate segment; and/or wherein the moment of inertia along the first direction (Y-Y) of said second cross-section of the second segment is smaller than the moment of inertia along the second direction (Z-Z) of said second cross-section of the second segment.

6. The annuloplasty prosthesis device of claim 1, wherein said second direction (Z-Z) forms a predetermined angle (α) with said lying plane (X-Y); and/or wherein said predetermined angle (α) is comprised from 20° to 160°.

7. The annuloplasty prosthesis device of claim 1, wherein said first arcuate segment has a first segment concavity always facing a same direction along the entire longitudinal extension of said first arcuate segment; and/or wherein said first segment concavity faces towards a prosthesis lumen; and/or wherein said at least one second segment is arcuate; and/or wherein said body of the annuloplasty prosthesis device further comprises a first joining segment and a second joining segment opposite said first joining segment, wherein each joining segment connects said first arcuate segment and said at least one second segment together along said longitudinal direction (X-X) of the body of the annuloplasty prosthesis device; and/or wherein said second segment, said first joining segment and said second joining segment describe an open annular path along the longitudinal direction (X-X) defining a saddle portion comprising at least one change of concavity; and/or wherein said saddle portion, when under undeformed conditions, substantially lies on the lying plane (X-Y); and/or wherein said saddle portion extends out of the lying plane (X-Y).

8. The annuloplasty prosthesis device of claim 1, wherein:

said body describes a closed ring surrounding said prosthesis lumen;

or said body describes an open annular path, embracing said prosthesis lumen.

9. The annuloplasty prosthesis device of claim 1 comprising a core conferring rigidity and flexibility properties to the body of the annuloplasty prosthesis device; and/or wherein said core has a cross-section, transverse to the longitudinal direction (X-X), substantially of the same shape and size along the whole longitudinal extension of said body of the annuloplasty prosthesis device.

10. The annuloplasty prosthesis device of claim 9, wherein said core has a cross-section of a substantially rectangular shape having a first cross-section dimension and a second cross-section dimension, substantially orthogonal to said first cross-section dimension, wherein said first cross-section dimension is greater than said second cross-section dimension.

11. The annuloplasty prosthesis device of claim 9, wherein said core is made in single piece.

12. The annuloplasty prosthesis device of claim 9, further comprising a coating covering said core; and/or wherein said core is made of a tubular element, made of nitinol and/or another biocompatible material, processed by means of machining, to form a plurality of cells or meshes following one another in the longitudinal direction (X-X) along at least one portion of the longitudinal extension of said body, and preferably along the whole longitudinal extension of said body, and even more preferably, said first arcuate segment and said second segment each comprise cells or meshes adapted to provide a directional selective rigidity; and/or wherein said core is made of a plurality of wires or threads intertwined to form a strand; and/or wherein each of said first arcuate segment and said second segment comprises means for fastening adjacent wires or threads of said plurality of wires or threads to prevent relative sliding thereof locally in a certain direction; and/or wherein said core is made of a plurality of lamellae or bands or ribbons adjacent to one another; and/or wherein each of said first arcuate segment and said second segment comprises means for fastening adjacent lamellae or bands or ribbons of said plurality of lamellae or bands or ribbons to prevent relative sliding thereof locally in a certain direction; and/or wherein said core is formed partially by lamellae or bands or ribbons, and/or partially of wires or threads intertwined to form a strand, and/or partially of adjacent meshes or cells, and/or combinations thereof.

13. The annuloplasty prosthesis device of claim 1, wherein:

said first arcuate segment is at least partially formed by a leaf spring, so as to be adapted to elastically bias for remodeling a rear portion of the native annulus; and/or wherein said second segment is at least partially formed by a leaf spring, so as to be adapted to elastically bias for remodeling a front portion of the native annulus.

14. An annuloplasty prosthesis device, suitable for native annulus remodeling, comprising a body having a shape of at least one portion of a ring defining a longitudinal direction (X-X), coincident with or locally parallel to the longitudinal development direction of said body, wherein:

said body comprises a first arcuate segment and at least one second segment, opposite said first arcuate segment;

said first arcuate segment is flexible in a first direction (Y-Y), locally transverse to the longitudinal direction (X-X) along said first arcuate segment, so as to be deformable in bending along said first direction (Y-Y);

said first arcuate segment defines a lying plane (X-Y) substantially parallel to both the longitudinal direction (X-X) and the first direction (Y-Y);

said at least one second segment is more rigid under flexion than said first arcuate segment in said lying plane (X-Y); and said second segment is flexible in a second direction (Z-Z), transverse to the lying plane (X-Y), so as to be deformable in bending along said second direction (Z-Z), providing directional selective flexibility to said annuloplasty prosthesis device for the purpose of guiding the native annulus remodeling;

wherein a cross-section of said first arcuate segment and a cross-section of said second segment have same shape and area measurement and are mutually inclined by a twist angle (β).

* * * * *